United States Patent
Bhullar et al.

(10) Patent No.: US 6,767,440 B1
(45) Date of Patent: Jul. 27, 2004

(54) BIOSENSOR

(75) Inventors: Raghbir S. Bhullar, Indianapolis, IN (US); John T. Austera, Indianapolis, IN (US); Brian S. Hill, Avon, IN (US); Christopher D. Wilsey, Carmel, IN (US)

(73) Assignee: Roche Diagnostics Corporation, Indianapolis, IN (US)

( * ) Notice: Subject to any disclaimer, the term of this patent is extended or adjusted under 35 U.S.C. 154(b) by 383 days.

(21) Appl. No.: 09/840,843

(22) Filed: Apr. 24, 2001

(51) Int. Cl.[7] .......................................... G01N 27/327
(52) U.S. Cl. ............................. 204/403.01; 204/403.14
(58) Field of Search ..................... 204/403.01, 403.02, 204/403.14; 422/82.01, 82.02, 82.03

(56) References Cited

U.S. PATENT DOCUMENTS

| | | |
|---|---|---|
| 4,963,814 A | 10/1990 | Parks et al. |
| 4,968,400 A * | 11/1990 | Shimomura et al. ........ 257/253 |
| 4,999,582 A | 3/1991 | Parks et al. |
| 4,999,632 A | 3/1991 | Parks |
| 5,018,527 A * | 5/1991 | Pfab et al. .................. 600/348 |
| 5,098,545 A * | 3/1992 | Patko ..................... 204/403.03 |
| 5,243,516 A | 9/1993 | White |
| 5,352,351 A | 10/1994 | White et al. |
| 5,366,609 A | 11/1994 | White et al. |
| 5,405,511 A | 4/1995 | White et al. |
| 5,413,690 A | 5/1995 | Kost et al. |
| 5,438,271 A | 8/1995 | White et al. |
| 5,762,770 A | 6/1998 | Pritchard et al. |
| 5,798,031 A | 8/1998 | Charlton et al. |
| 5,997,817 A | 12/1999 | Crismore et al. |
| 6,071,392 A * | 6/2000 | Yamamoto et al. ...... 204/403.1 |
| 6,132,683 A * | 10/2000 | Sugihara et al. .......... 422/82.01 |
| 6,212,416 B1 * | 4/2001 | Ward et al. .................. 600/345 |
| 6,432,720 B2 * | 8/2002 | Chow .......................... 436/180 |

FOREIGN PATENT DOCUMENTS

| | | |
|---|---|---|
| EP | 1 195 441 A1 | 4/2002 |
| WO | WO 99/58709 | 11/1999 |
| WO | WO 00/73778 | 12/2000 |
| WO | WO 00/73785 | 12/2000 |
| WO | WO 01/25775 A1 | 4/2001 |

OTHER PUBLICATIONS

LPKF MicrolineLaser II, LPKF Laser & Electronics AG; LPKF; Art.–Nr. 107645–2 (01/00) (2pp.).
Microline Solutions, LPKF Laser & Electronics AG; LPKF; Art.–Nr. 107658–1 (01/00) (4pp.).

* cited by examiner

Primary Examiner—Kaj K. Olsen
(74) Attorney, Agent, or Firm—Jill L. Woodburn

(57) ABSTRACT

A biosensor is provided in accordance with the present invention. The biosensor includes an electrode support substrate, electrodes positioned on the electrode support substrate, a sensor support substrate coupled to the electrode support substrate, and electrically conductive tracks positioned on the sensor support substrate. Each track is in electrical communication with one of the electrodes.

24 Claims, 4 Drawing Sheets

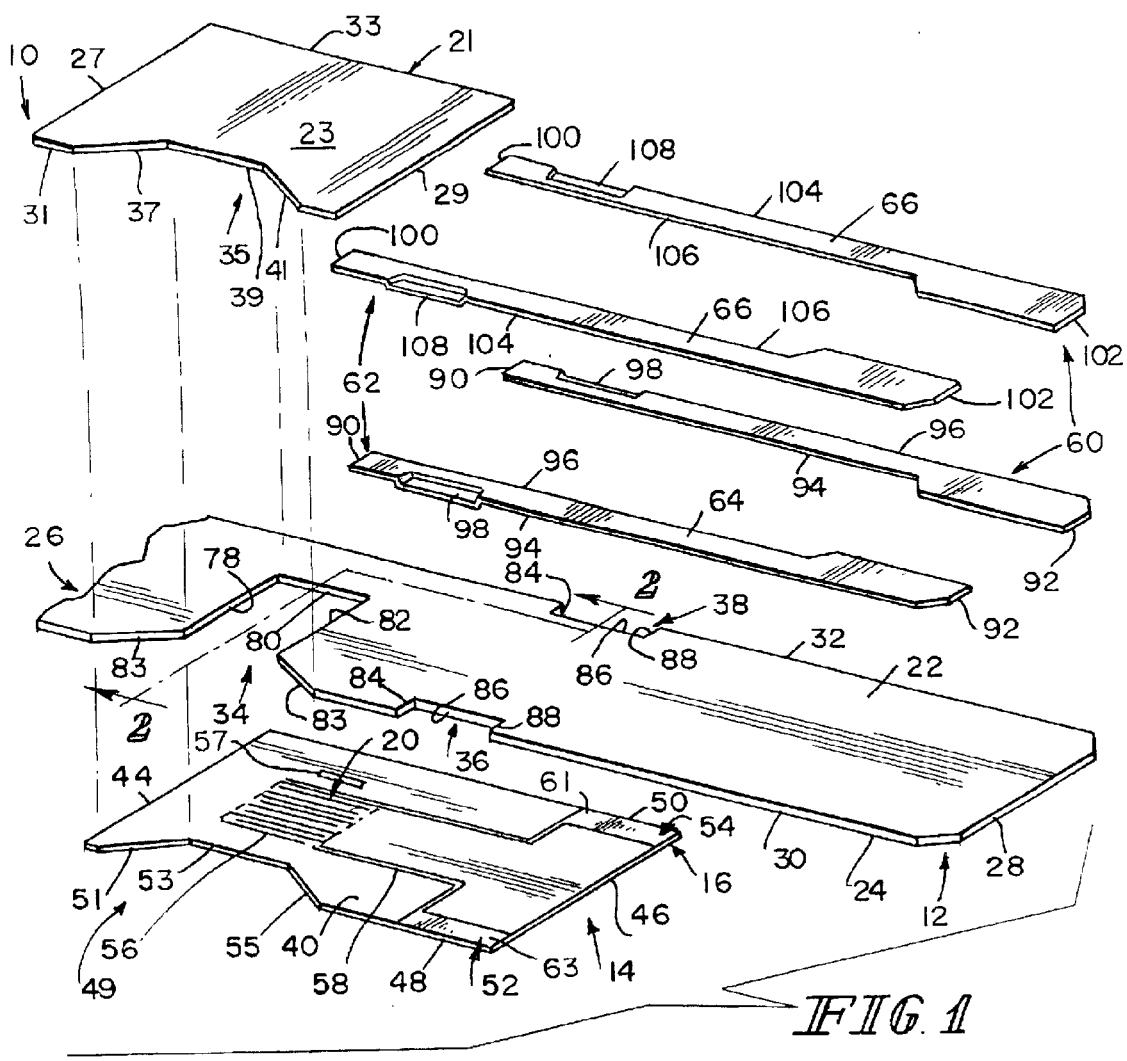
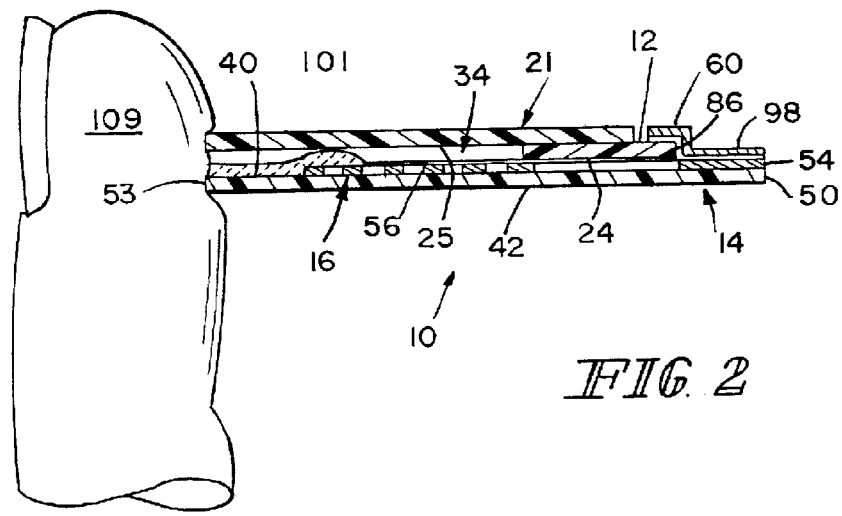
FIG. 1
FIG. 2

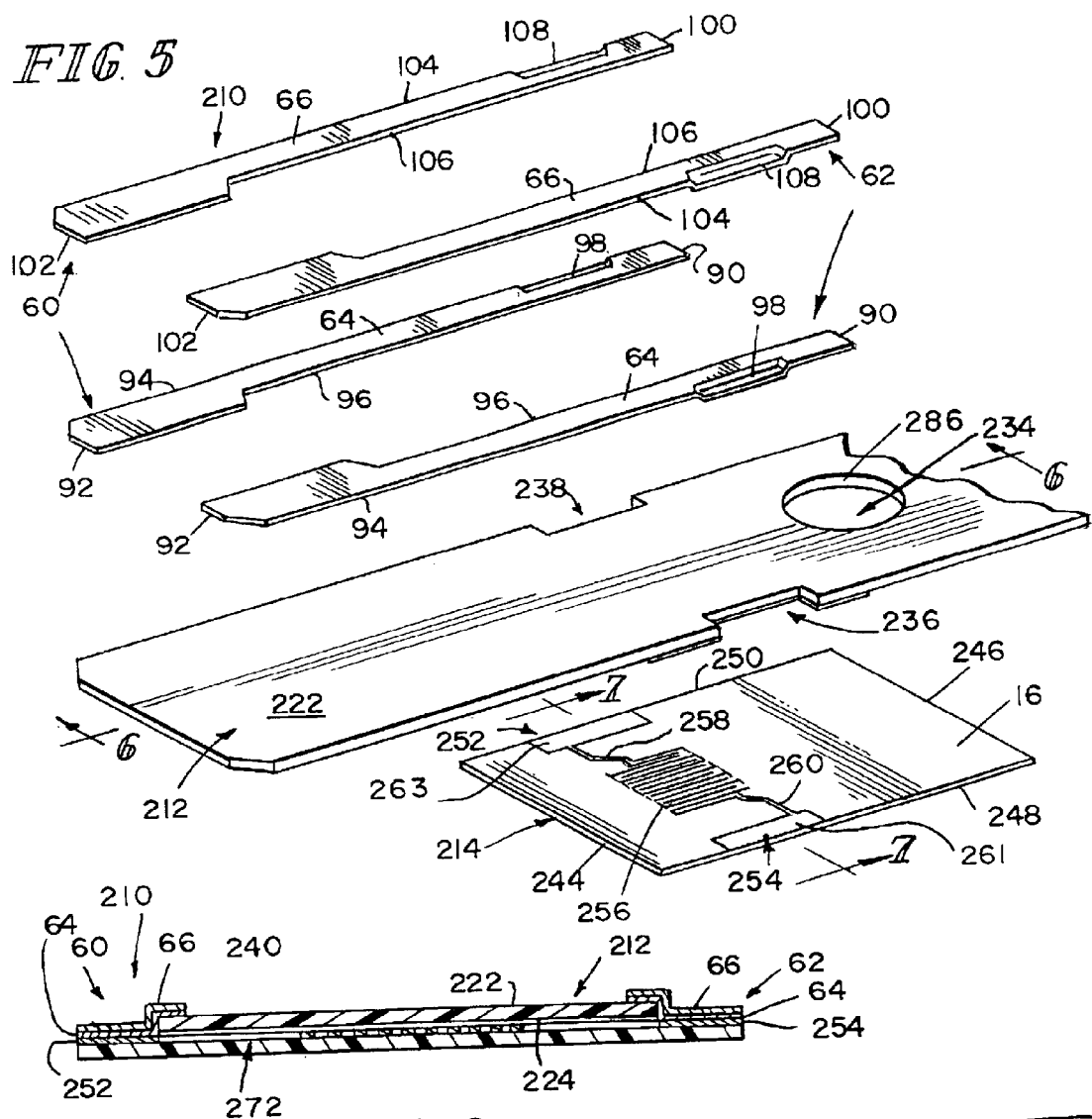
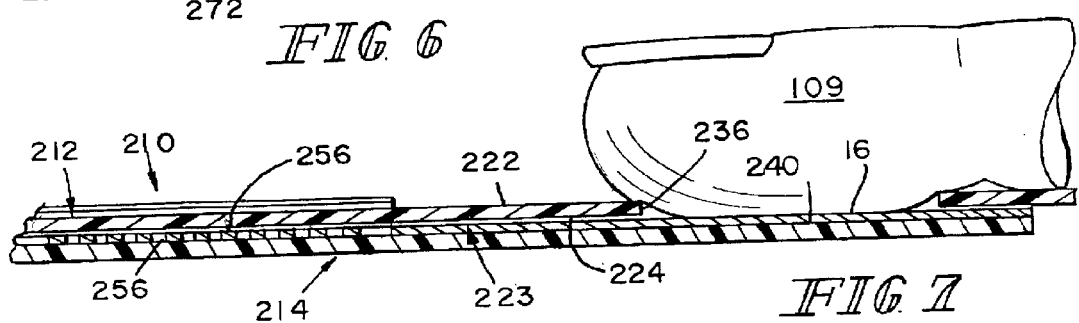

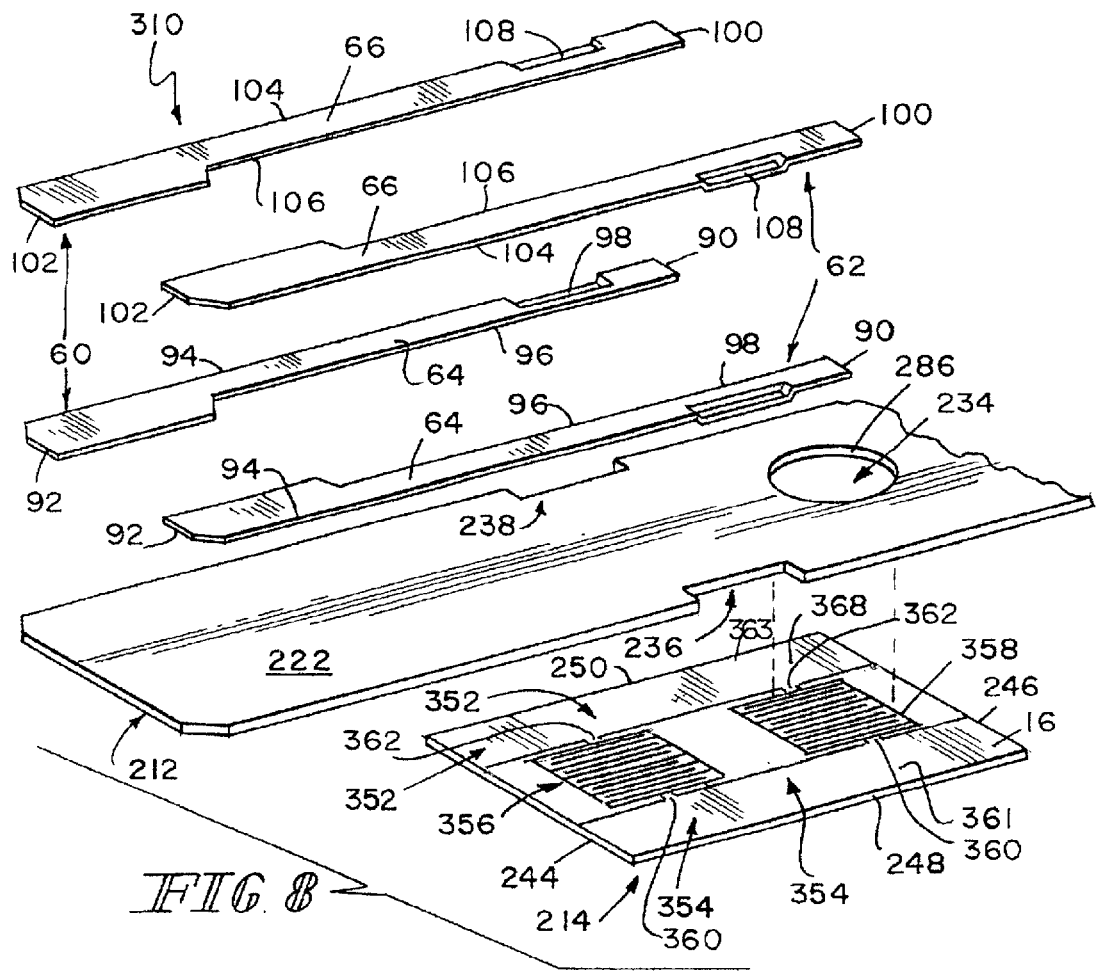
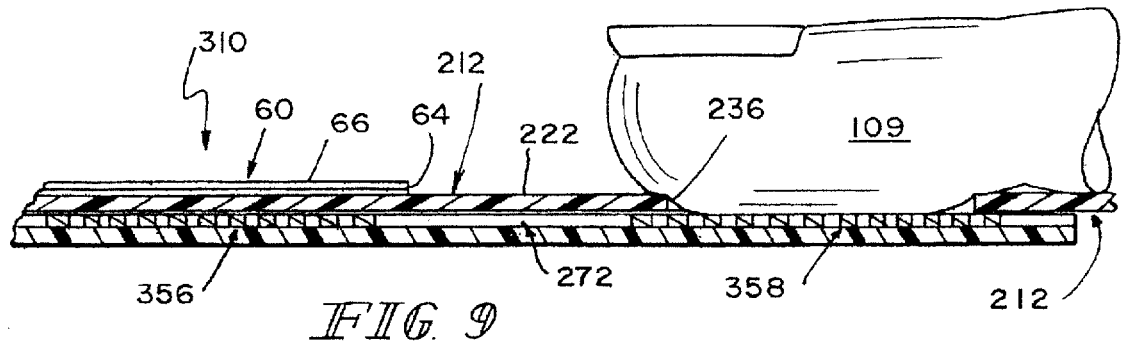

ic examples of suitable electrical conductors include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, conductor 16 includes gold, palladium, aluminum, titanium, platinum, and indium tin oxide, and most preferably conductor 16 includes gold. Conductor 16 is isolated from the rest of the metallic layer by laser ablation. Preferably conductor 16 is formed by removing the conductive material from an area extending around the electrodes. It is appreciated that electrical conductor 16 may be isolated by a variety of techniques including, but not limited to chemical etching, laser ablation of multiple tracks in the metallic layer, scribing the metallic layer, or otherwise removing the conductivity in specific areas of the metallic layer to create electrodes.

BIOSENSOR

FIELD OF THE INVENTION

The present invention relates to a biosensor, more particularly to an electrochemical biosensor with a hybrid electrode.

BACKGROUND AND SUMMARY OF THE INVENTION

Electrochemical biosensors are known. They have been used to determine the concentration of various analytes from biological samples, particularly from blood. Electrochemical biosensors are described in U.S. Pat. Nos. 5,413,690; 5,762,770; 5,798,031; and 5,997,817 the disclosure of each of which is expressly incorporated herein by reference.

According to one aspect of the present invention an electrochemical biosensor is provided. The biosensor comprises an electrode support substrate, electrodes positioned on the electrode support substrate, a sensor support substrate coupled to the electrode support substrate, and electrically conductive tracks positioned on the sensor support substrate, each track being in electrical communication with one of the electrodes.

According to another aspect of the present invention an electrochemical biosensor is provided. The biosensor comprises a metallized electrode support substrate defining an electrode array and leads extending from the array, a sensor support substrate coupled to the electrode support substrate, the sensor support substrate being formed to include notches and an opening, at least a portion of each notch being aligned with one lead and the opening being spaced-apart from the leads, and electrically-conductive tracks positioned on the sensor support substrate. Each track extends across one of the notches and into engagement with one lead.

According to still another aspect of the present invention a method of forming a biosensor is provided. The method comprises the steps of providing a metallized electrode support substrate and a sensor support substrate, ablating the electrode support substrate to form electrodes, coupling the sensor support substrate to the electrode support substrate, and positioning spaced-apart electrically conductive tracks across the sensor support substrate so that each track is in electrical communication with one electrode.

Additional features of the invention will become apparent to those skilled in the art upon consideration of the following detailed description of the preferred embodiment exemplifying the best mode of carrying out the invention as presently perceived.

BRIEF DESCRIPTION OF THE DRAWINGS

The detailed description particularly refers to the accompanying figures in which:

FIG. 1 is an exploded assembly view of a biosensor in accordance with the present invention, showing the biosensor including an electrode support substrate, laser-ablated electrodes on the electrode support substrate, a sensor support substrate, electrically-conductive tracks formed to be positioned on the sensor support substrate and in engagement with the laser-ablated electrodes, and a cover substrate.

FIG. 2 is a cross-sectional view taken through lines 2—2 of FIG. 1 showing a liquid blood sample entering the biosensor.

FIG. 5 is an exploded assembly view of a biosensor in accordance with another aspect of the present invention.

FIG. 6 is a cross-sectional view taken through lines 6—6 of FIG. 5.

FIG. 7 is a cross-sectional view taken through lines 7—7 of FIG. 5.

FIG. 8 is an exploded assembly view of a biosensor in accordance with another aspect of the present invention.

FIG. 9 is a cross-sectional view of FIG. 8.

DETAILED DESCRIPTION OF THE DRAWINGS

Figure 3:
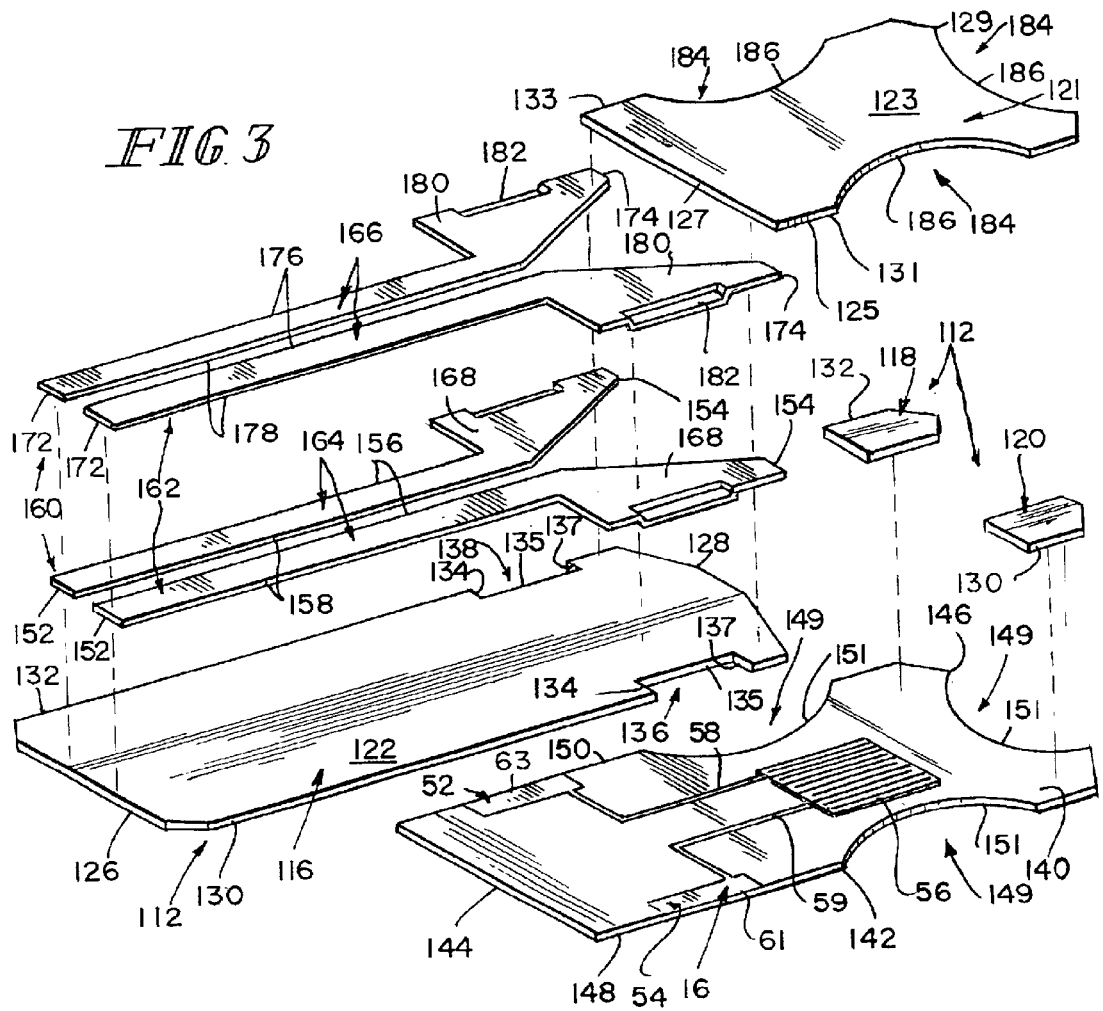
FIG. 3 is an exploded assembly view of a biosensor in accordance with another aspect of the present invention.

The present invention relates to a biosensor and a method for manufacturing a biosensor that provides a manufacturer with flexibility in electrode design variation. The biosensor uses a high-end process such as laser ablation to produce sensitive parts of the biosensor and uses a screen-printing process to make meter contacts. Thus, by simply changing a sensor support substrate and/or a cover substrate as well as the electrode ablation pattern multiple products can be produced from the same manufacturing system to meet market needs. Various aspects of the invention are presented in FIGS. 1–9, which are not drawn to scale and wherein like components in the several views are numbered alike.

FIGS. 1–2 illustrate an aspect of the invention in the form of a biosensor 10 having a sensor support substrate 12, an electrode support substrate 14, a first electrical conductor 16 positioned on the electrode support substrate 14, an electrochemical reagent 20 positioned on first conductor 16, a first electrically-conductive track 60 and a second electrically-conductive track 62 each extending across the sensor support substrate 12, and a cover substrate 21. Biosensor 10 is preferably rectangular in shape. It is appreciated, however, that biosensor 10 can assume any number of shapes in accordance with this disclosure. Biosensor 10 is preferably produced from rolls of material, however, it is understood that biosensor 10 can be constructed from individual sheets in accordance with this disclosure. Thus, the selection of materials for the construction of biosensor 10 necessitates the use of materials that are sufficiently flexible for roll processing, but which are still rigid enough to give a useful stiffness to finished biosensor 10.

The electrode support substrate 14 is shown in FIGS. 1 and 2, and includes a top surface 40 facing sensor support substrate 12 and a bottom surface 42. In addition, electrode support substrate 14 has opposite ends 44, 46 and opposite edges 48, 50 extending between ends 44, 46. Edge 48 includes a notch 49 formed therein. Notch 49 is defined by boundaries 51, 53, 55. In addition, a vent opening 57 extends between top and bottom surfaces 40, 42. Vent opening 57 may have a wide variety of shapes and sizes in accordance with this invention. Electrode support substrate 14 is generally rectangular in shape, it is appreciated, however, that support may be formed in a variety of shapes and sizes and notch 49 can be positioned in a variety of locations in accordance with this disclosure. Electrode support substrate 14 is formed from a flexible polymer and preferably from a polymer such as a polyester or polyimide, polyethylene naphthalate (PEN). A non-limiting example of a suitable PEN is 5 mil thick KALADEX®, a PEN film commercially available from E.I. DuPont de Nemours, Wilmington, Del., which is coated with gold by ROWO Coating, Henbolzhelm, Germany.

Electrical conductor 16 is created or isolated on top surface 40 of electrode support substrate 14. Non-limiting examples of a suitable electrical conductor 16 include aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, electrical conductor 16 is selected from the following materials: gold, platinum, palladium, iridium, or alloys of these metals, since such noble metals and their alloys are unreactive in biological systems. Most preferably, electrical conductor 16 is gold.

Conductor 16 is disrupted to create electrodes 52, 54 on electrode support substrate 14 that are isolated from the rest of the electrically conductive surface by laser ablation. Techniques for forming electrodes on a surface using laser ablation are known. See, for example, U.S. patent application Ser. No. 09/411,940, filed Oct. 4, 1999, and entitled "LASER DEFINED FEATURES FOR PATTERNED LAMINATES AND ELECTRODE", the disclosure of which is expressly incorporated herein by reference. Preferably, electrodes 52, 54 are created by removing the electrical conductor 16 from an area extending around the electrodes.

Therefore, electrodes 52, 54 are isolated from the rest of the electrically-conductive material on electrode support substrate 14 by a gap having a width of about 25 $\mu$m to about 500 $\mu$m, preferably the gap has a width of about 100 $\mu$m to a about 200 $\mu$m. Alternatively, it is appreciated that electrodes 52, 54 may be created by laser ablation alone on electrode support substrate 14. It is appreciated that while laser ablation is the preferred method for forming electrodes 52, 54 given its precision and sensitivity, other techniques such as lamination, screen-printing, or photolithography may be used in accordance with this disclosure.

Electrodes 52, 54 cooperate with one another to define an electrode array 56 and leads 58, 59 that extend away from array 56. As shown in FIG. 1, leads 58, 59 extend from array 56 to contact pads 61, 63 respectively. Contact pads 61, 63 are located at respective edges 48, 50. It is appreciated that array 56 and contact pads 61, 63 can have a variety of shapes and sizes and leads 58, 59 can be formed to have many lengths and extend to a variety of locations so that contact pads 61, 63 can be located on electrode support substrate 14.

Multi-electrode set arrangements are also possible in accordance with this disclosure. It is appreciated that the number of electrodes, as well as the spacing between the electrodes may vary in accordance with this disclosure and that a number of arrays may be formed (FIGS. 8–9) as will be appreciated by one of skill in the art.

Sensor support substrate 12 of biosensor 10 includes a first surface 22 and an opposite second surface 24 facing electrode support substrate 14. See FIGS. 1 and 2. In addition, sensor support substrate 12 has opposite ends 26, 28 and edges 30, 32 extending between ends 26, 28. An opening 34 extends between first and second surfaces 22, 24 as shown in FIG. 1. In addition, notches 36, 38 are formed in edges 30, 32 respectively, which are spaced-apart from opening 34. As shown in FIG. 1, opening 34 is defined by boundaries 78, 80, 82 and tapers 843 that extend between edge 30 and boundaries 78, 82. In addition, notches 36, 38 are each defined by boundaries 84, 86, 88.

When sensor support substrate 12 is coupled to electrode support substrate 14, tapers 83 are in general alignment with boundaries 51, 55 of electrode support substrate 14 such that opening 34 exposes electrode array 56 and reagent 20. In addition, notches 36, 38 are in general alignment with contact pads 61, 63 of electrodes 52, 54. It is appreciated that notches 36, 38 can be located in a number of locations and formed in a variety of shapes and sizes in sensor support substrate 12 in accordance with this disclosure. It is also appreciated that sensor support substrate 12 may be formed without notches in accordance with this disclosure, so long as tracks 60, 62 are in electrical communication with electrodes 52, 54. Sensor support substrate 12 is formed of a flexible polymer and preferably from a polymer such as polyester. A non-limiting example of a suitable polymer is 7 mil thick ST505 MELENEX® polyester film commercially available from E.I. DuPont de Nemours, Wilmington, Del.

Additionally, while not illustrated, surface 24 of sensor support substrate 12 is coated with an adhesive. Preferably, sensor support substrate 12 is coupled to electrode support substrate 14 with a thermoset adhesive. A non-limiting example of such an adhesive is a blend of item #38-8569 (5% wt./wt. isocyanate) and item #38-8668 (95% wt./wt. polyurethane), both commercially available from National Starch& Chemical, a Member of ICI Group, Bridgewater, N.J. It is appreciated that substrate may be coupled to electrode support substrate 14 using a wide variety of commercially available adhesives or with welding (heat or ultrasonic) in accordance with this disclosure. It is also appreciated that first surface 22 of sensor support substrate 12 may be printed with, for example, product labeling or instructions for use in accordance with this disclosure.

Referring again to FIG. 1, first and second tracks 60, 62 formed to be positioned on first surface 22 of sensor support substrate 12. Tracks 60, 62 each extend from end 28 and across one of the notches 36, 38. While track 60, notch 38, and electrode 54 will be discussed hereafter, it is appreciated that unless indicated otherwise, the description applies to track 62, notch 36, and electrode 52 as well. Track 60 includes a first layer 64 and a second layer 66. Preferably first layer 64 includes opposite ends 90, 92 and edges 94, 96 extending between ends 90, 92. As shown in FIGS. 1 and 2, upon assembly of biosensor, a portion 98 of first layer 64 extends downwardly from first surface 22 of sensor support substrate 12 into notch 38 and engages electrode 54. In this manner, first layer 64 is in electrical communication with electrodes 52, 54 of electrode support substrate 14. Second layer 66 of tracks 60 includes opposite ends 100, 102 and edges 104, 106 extending between ends 100, 102. In addition, a portion 108 of second layer 66 is aligned with portion 98 of first layer 64. Thus, second layer 66 is in electrical communication with electrodes 52, 54 via the first layer 64 upon assembly of biosensor 10.

Tracks 60, 62 are preferably screen-printed onto sensor support substrate 12. The method of forming tracks 60, 62, however, is not limited. While direct contact between track 60 and electrode 54 is illustrated and described, it is appreciated track 60 and electrode 54 may not be in direct contact with one another so long as there is an electrical connection between the two, i.e. vias or other methods appreciated by those skilled in the art.

Non-limiting examples of suitable electrical conductors for first and second layers 64, 66 include aluminum, carbon (such as graphite), cobalt, copper, gallium, gold, indium, iridium, iron, lead, magnesium, mercury (as an amalgam), nickel, niobium, palladium, platinum, rhenium, rhodium, selenium, silicon (such as highly doped polycrystalline silicon), silver, tantalum, tin, titanium, tungsten, uranium, vanadium, zinc, zirconium, mixtures thereof, and alloys, oxides, or metallic compounds of these elements. Preferably, first layer 64 is silver ink, a non-limiting example of which is ELECTRODAG® 427ss, commercially available from Acheson Colloids Company, Port Huron, Mich. Second layer 66 is preferably a carbon ink, a non-limiting example of which is a conductive screen-printable ink of finely divided graphite particles dispersed in a thermoplastic resin such as ELECTRODAG® 423ss or ELECTRODAG® PM-003A, both commercially available from Acheson Colloids Company, Port Huron, Mich.

Cover substrate 21 is coupled to first surface 22 of sensor support substrate 12. Cover substrate 21 includes a first surface 23 and a second surface 25 facing sensor support substrate 12. In addition, cover substrate 21 includes opposite ends 27, 29 and edges 31, 33 extending between the ends 27, 29. Edge 31 includes a notch 35. Notch 35 is defied by boundaries 37, 39, 41. When biosensor 10 is assembled, cover substrate 21 cooperates with boundaries 78, 80, 82 of opening and sensor support substrate 12 to define a capillary channel.

Cover substrate 21 is generally rectangular in shape, it is appreciated, however, that the cover substrate may be formed in a variety of shapes and sizes in accordance with this disclosure. Cover substrate 21 is formed from a flexible polymer and preferably from a polymer such as a polyester or polyimide. A non-limiting example of a suitable polymer is 3 mil thick clear MELINEX ST-505, coated with 3M fast-bond #30NF, thermoset adhesive. This adhesive is treated with 7% wt./wt. (Triton X-100 detergent).

Electrochemical reagent 20 is positioned on array 56. Reagent 20 provides electrochemical probes for specific analytes. The choice of specific reagent 20 depends on the specific analyte or analytes to be measured, and are well known to those of ordinary skill in the art. An example of a reagent that may be used in biosensor 10 of the present invention is a reagent for measuring glucose from a whole blood sample. A non-limiting example of a reagent for measurement of glucose in a human blood sample contains 62.2 mg polyethylene oxide (mean molecular weight of 100–900 kilo Daltons), 3.3 mg NATROSOL 244M, 41.5 mg AVICEL RC-591 F, 89.4 mg monobasic potassium phosphate, 157.9 mg dibasic potassium phosphate, 437.3 mg potassium ferricyanide, 46.0 mg sodium succinate, 148.0 mg trehalose, 2.6 mg TRITON X-100 surfactant, and 2,000 to 9,000 units of enzyme activity per gram of reagent. The enzyme is prepared as an enzyme solution from 12.5 mg coenzyme PQQ and 1.21 million units of the apoenzyme of quinoprotein glucose dehydrogenase. This reagent is further described in U.S. Pat. No. 5,997,817, the disclosure of which is expressly incorporated herein by reference.

Non-limiting examples of enzymes and mediators that may be used in measuring particular analytes in biosensor 10 are listed below in Table 1.

TABLE 1

| Analyte | Enzymes | Mediator (Oxidized Form) | Additional Mediator |
|---|---|---|---|
| Glucose | Glucose Dehydrogenase and Diaphorase | Ferricyanide | |
| Glucose | Glucose-Dehydrogenase (Quinoprotein) | Ferricyanide | |
| Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| HDL Cholesterol | Cholesterol Esterase and Cholesterol Oxidase | Ferricyanide | 2,6-Dimethyl-1,4-Benzoquinone 2,5-Dichloro-1,4-Benzoquinone or Phenazine Ethosulfate |
| Triglycerides | Lipoprotein Lipase, Glycerol Kinase, and Glycerol-3-Phosphate Oxidase | Ferricyanide or Phenazine Ethosulfate | Phenazine Methosulfate |
| Lactate | Lactate Oxidase | Ferricyanide | 2,6-Dichloro-1,4-Benzoquinone |
| Lactate | Lactate Dehydrogenase and Diaphorase | Ferricyanide Phenazine Ethosulfate, or Phenazine Methosulfate | |
| Lactate Dehydrogenase | Diaphorase | Ferricyanide | Phenazine Ethosulfate, or Phenazine Methosulfate |
| Pyruvate | Pyruvate Oxidase | Ferricyanide | |
| Alcohol | Alcohol Oxidase | Phenylenediamine | |
| Bilirubin | Bilirubin Oxidase | 1-Methoxy-Phenazine Methosulfate | |
| Uric Acid | Uricase | Ferricyanide | |

In some of the examples shown in Table 1, at least one additional enzyme is used as a reaction catalyst. Also, some of the examples shown in Table 1 may utilize an additional mediator, which facilitates electron transfer to the oxidized form of the mediator. The additional mediator may be provided to the reagent in lesser amount than the oxidized form of the mediator. While the above assays are described, it is contemplated that current, charge, impedance, conductance, potential, or other electrochemically indicated property of the sample might be accurately correlated to the concentration of the analyte in the sample with biosensor 10 in accordance with this disclosure.

A plurality of biosensors 10 are typically packaged in a vial, usually with a stopper formed to seal the vial. It is appreciated, however, that biosensors 10 may be packaged individually, or biosensors can be folded upon one another, rolled in a coil, stacked in a cassette magazine, or packed in blister packaging.

Biosensor 10 is used in conjunction with the following:
1. a power source in electrical connection with tracks 60, 62 and capable of supplying an electrical potential difference between electrodes 52, 54 sufficient to cause diffusion limited electro-oxidation of the reduced form of the mediator at the surface of the working electrode; and
2. a meter in electrical connection with tracks 60, 62 and capable of measuring the diffusion limited current produced by oxidation of the reduced form of the mediator with the above-stated electrical potential difference is applied.

The meter will normally be adapted to apply an algorithm to the current measurement, whereby an analyte concentration is provided and visually displayed. Improvements in such power source, meter, and biosensor system are the subject of commonly assigned U.S. Pat. No. 4,963,814, issued Oct. 16, 1990; U.S. Pat. No. 4,999,632, issued Mar. 12, 1991; U.S. Pat. No. 4,999,582, issued Mar. 12, 1991; U.S. Pat. No. 5,243,516, issued Sep. 7, 1993; U.S. Pat. No. 5,352,351, issued Oct. 4, 1994; U.S. Pat. No. 5,366,609, issued Nov. 22, 1994; White et al., U.S. Pat. No. 5,405,511, issued Apr. 11, 1995; and White et al., U.S. Pat. No. 5,438,271, issued Aug. 1, 1995, the disclosures of each of which are expressly hereby incorporated by reference.

Many fluid samples may be analyzed. For example, human body fluids such as whole blood, plasma, sera, lymph, bile, urine, semen, cerebrospinal fluid, spinal fluid, lacrimal fluid and stool specimens as well as other biological fluids readily apparent to one skilled in the art may be measured. Fluid preparations of tissues can also be assayed, along with foods, fermentation products and environmental substances, which potentially contain environmental contaminants. Preferably, whole blood is assayed with this invention.

A non-limiting method of manufacturing biosensor 10 is described below. A roll of thermoset-adhesive coated sensor support substrate material is fed into a punching unit where openings 34 and notches 36, 38 are punched out. It is appreciated that a separate coating step can be performed before the sensor support material substrate is fed into the punching unit. It is appreciated that the sensor support substrate pre-coated with a heat-sealable adhesive is also commercially available.

In a separate process, a roll of metallized electrode support material is fed through guide rolls into an ablation/washing and drying station. A laser system capable of ablating electrode support substrate 14 is known to those of ordinary skill in the art. Non-limiting examples of which include excimer lasers, with the pattern of ablation controlled by mirrors, lenses, and masks. A non-limiting example of such a custom fit system is the LPX-300 or LPX-200 both commercially available from LPKF Laser Electronic GmbH, of Garbsen, Germany.

In the laser ablation station, the metallic layer of the metallized film is ablated in a pre-determined pattern, to form a ribbon of isolated electrode sets on the electrode support material. To ablate electrodes in 50 nm thick gold conductor, 90 mJ/cm$^2$ energy is applied. It is appreciated, however, that the amount of energy required may vary from material to material, metal to metal, or thickness to thickness. The ribbon is then passed through more guide rolls, with a tension loop and through an inspection system where both optical and electrical inspection can be made. The system is used for quality control in order to check for defects. In that station, vent holes are also punched through the electrode support substrate material.

The sensor support substrate material then fed into a cutting/lamination station along with the electrode support substrate material. The electrode support substrate material cut into strips and then aligned with the opening and notches of the sensor support substrate. The electrode support substrate is coupled to the sensor support substrate by a pressure and heat-sealing lamination process. Specifically, the aligned material is rolled against either a hot plate or a heat roller to couple the sensor support substrate to the strips of the electrode support substrate material and form a sensor support/electrode support subassembly.

This sensor support/electrode support subassembly is then fed into a screen or stencil printer equipped with IR drying stations. The silver ink is applied as first electrically conductive tracks on the first surface 22 of the sensor support substrate 12. The silver ink is dried in a first IR dryer to cure the ink for approximately 2 minutes. Next, the carbon ink is applied as second electrically conductive tracts on the first electrically conductive tracks. The carbon ink is also cured in the second IR drier for approximately 2 minutes.

Next, the sensor support/electrode support subassembly is fed into a reagent dispensing station. The reagent 20 that has been compounded is fed into a dispensing station where it is applied in a liquid form to the center of the array 56. Reagent application techniques are well known to one of ordinary skill in the art as described in U.S. Pat. No. 5,762,770, the disclosure of which is expressly incorporated herein by reference. It is appreciated that the reagent may be applied to the array 56 in a liquid or other form and dried or semi-dried onto the array 56 in accordance with this disclosure.

A roll of cover substrate material is fed into a cutting/lamination station along with the sensor support/electrode support subassembly. The cover substrate material is cut into strips and then aligned with the opening of the sensor support substrate. The cover substrate is coupled to the sensor support substrate by a pressure and heat-sealing lamination process. Specifically, the aligned material is rolled against either a hot plate or a heat roller to couple the sensor support substrate to the strips of the cover substrate material.

Next, the assembled material is fed into a sensor punch and packaging station. In this station, the notches 35, 49 are formed in the cover substrate 21 and the electrode support substrate 14 respectively as are the tapers 83 leading to the opening 34 in the sensor support substrate 12. The assembled material is punched to form individual biosensors 10, which are sorted and packed into vials, each closed with a stopper, to give packaged biosensor strips.

In use, a user of biosensor 10 places a finger 109 having a blood collection incision against boundaries 39, 53 of notches 35, 49. Capillary forces pull a liquid blood sample 101 flowing from the incision into opening 34 and through the capillary channel across reagent 20 and array 56. The liquid blood sample 101 wets the reagent 20 and engages electrode array 56, where the electrochemical reaction takes place.

In use, after the reaction is complete, a power source (e.g., a battery) applies a potential difference between tracks 60, 62. The voltage travels through layers 66, 64 and therefore between tracks 52, 54. When the potential difference is applied, the amount of oxidized form of the mediator at the auxiliary electrode and the potential difference must be sufficient to cause diffusion-limited electro-oxidation of the reduced form of the mediator at the surface of the working electrode. A current measuring meter (not shown) measures the diffusion-limited current generated by the oxidation of the reduced form of the mediator at the surface of the working electrode.

The measured current may be accurately correlated to the concentration of the analyte in sample when the following requirements are satisfied:

1. The rate of oxidation of the reduced form of the mediator is governed by the rate of diffusion of the reduced form of the mediator to the surface of the working electrode.
2. The current produced is limited by the oxidation of reduced form of the mediator at the surface of the working electrode.

Figure 4:
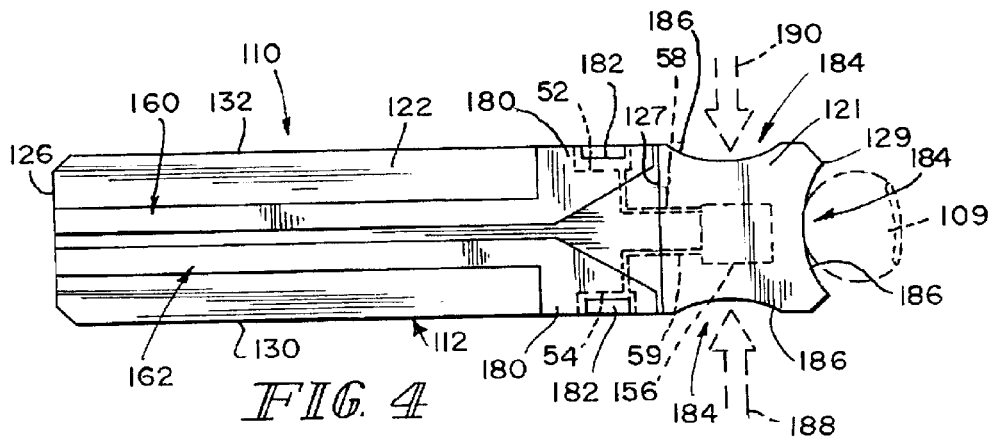
FIG. 4 is a plan view of the biosensor of FIG. 3.

FIGS. 3–4 illustrate an aspect of the invention in the form of a biosensor 110 having a sensor support substrate 112, an electrode support 114, the first electrical conductor 16 on the support 114, reagent (not shown) positioned on first conductor 16, a first electrically-conductive track 160 and a second electrically-conductive track 162 each extending across the support 112, and a cover 121. Biosensor 110 is preferably rectangular in shape. It is appreciated, however, that biosensor 110 can assume any number of shapes in accordance with this disclosure. Biosensor 110 is preferably produced from rolls of material. Thus, the selection of materials for the construction of biosensor 110 necessitates the use of materials that are sufficiently flexible for roll processing, but which are still rigid enough to give a useful stiffness to finished biosensor 110.

Support 114 includes a top surface 140 facing sensor support substrate 112 and a bottom surface 142. In addition, support 114 has opposite ends 144, 146 and opposite edges 148, 150 extending between ends 144, 146. Edges 148, 150 and end 146 each include a notch 149 formed by a generally concave-shaped boundary 151. While three concave shaped notches are illustrated, it is appreciated that support can include greater or fewer than three notches and said notches can have a variety of shapes and sizes in accordance with this disclosure. Support 114 is generally rectangular in shape, it is appreciated however, that support may be formed in a variety of shapes and sizes in accordance with this disclosure. Support 114 is formed from materials similar to electrode support substrate 14.

Electrodes 52, 54 cooperate with one another to define electrode array 56 on surface 140 and leads 58, 59 that extend away from array 56 to respective contact pads 61, 63 at edges 148, 150. It is appreciated that leads 58, 59 be formed to have a variety of lengths and extend to a variety of locations so that contact pads 61, 63 can be located on electrode support substrate 114.

Sensor support substrate 112 of biosensor 110 includes a main portion 116 and two sensor support substrate elements 118, 120. Main portion 116 and sensor support substrate elements 118, 120 each include a first surface 122 and an opposite second surface 124 facing electrode support 114 and edges 130, 132. In addition, main portion 116 of sensor support substrate 112 has opposite ends 126, 128. Notches 136, 138 are formed in edges 130, 132 respectively and are each defined by boundaries 134, 135, 137.

As shown in FIG. 4, when sensor support substrate 112 is coupled to electrode support substrate 114, notches 136, 138 (as shown in FIG. 3) are in general alignment contact pads 61, 63 of electrodes 52, 54. It is appreciated that notches 136, 138 can be located in a number of locations in sensor support substrate 112 and have a variety of shapes and sizes in accordance with this disclosure, so long as notches 136, 138 are aligned, at least in part with contact pads 61, 63 when biosensor 110 is assembled. Sensor support substrate 112 is formed of materials similar to sensor support substrate 12 and surface 124 of main portion 116 and sensor support substrate elements 118, 120 are coated with adhesive similar to surface 24 of sensor support substrate 12. It is also appreciated that sensor support substrate 112 may be printed with, for example, product labeling or instructions for use in accordance with this disclosure.

Referring again to FIG. 3, first and second tracks 160, 162 formed to be positioned on first surface 122 of main portion 116. Tracks 160, 162 each extend from end 126 and across respective notch 138, 136. While track 160, notch 138, and electrode 52 will be discussed hereafter, it is appreciated that unless indicated otherwise, the description applies to track 162, notch 136, and electrode 54 as well. Track 160 includes a first layer 164 and a second layer 166. Preferably first layer 164 includes opposite ends 152, 154 and edges 156, 158 extending between ends 152, 154. In addition, first layer 164 includes a generally triangle-shaped contact area 168. When biosensor 110 is assembled, a portion of contact area 168 extends downwardly from first surface 122 of sensor support substrate 112 into notch 138 and engages contact pad 63 of electrode 52. In this manner, first layer 164 is in electrical communication with electrodes 52, 54 of support 114.

Second layer 166 of track 160 includes opposite ends 172, 174 and edges 176, 178 extending between ends 172, 174. In addition, second layer 166 includes a generally triangle-shaped contact area 180. A portion 182 of contact area 180 is aligned with the portion of contact area 168 that engages electrode 52. Second layer 166, upon assembly of biosensor 110 is in electrical communication with electrodes 52 via first layer 164. Materials suitable to construct first and second layers 164, 166 are similar to those used to construct layers 64, 66. In addition, while direct contact between track 160 and electrode 54 is illustrated and described, it is appreciated track 160 and electrode 54 may not be in direct contact with one another so long as there is an electrical connection between the two.

Cover 121 is coupled to first surface 122 of main portion 116 and sensor support substrate elements 118, 120. Cover 121 includes a first surface 123 and a second surface 125 facing sensor support substrate 112. In addition, cover 121 includes opposite ends 127, 129 and edges 131, 133 extending between the ends 127, 129. Edges 131, 133 and end 129 each include a notch 184 formed by a generally concave-shaped boundary 186. When biosensor 110 is assembled, end 127 of cover is positioned over main portion 116 of sensor support substrate 112. In addition, end 129 of cover 121 is mounted on sensor support substrate elements 118, 120 of sensor support substrate 112. Thus, three capillary channels are defined between cover 121 and electrode support 114 and intersect one another at array 56. The first channel has an opening at ends 129, 146 and is defined by cover 121, electrode support substrate 114, and sensor support substrate elements 118, 120. The second channel has an opening at edges 125, 148 and is defined by cover 121, electrode support substrate 114, sensor support substrate element 120, and end 128 of main portion 116. The third channel has an opening at edges 133, 150 and is defined by cover 121, electrode support substrate 114, sensor support substrate element 118, and end 128 of main portion 116.

Cover 121 is generally rectangular in shape, it is appreciated however, that cover 121 may be formed in a variety of shapes and sizes in accordance with this disclosure. Cover 121 is formed from materials similar to cover substrate 21 and is coupled to electrode support substrate 114 with an adhesive similar to the adhesive used to couple cover substrate 21 to electrode support substrate 14. In addition, it is appreciated that cover 121 may be formed with greater or fewer than three notches and said notches can have a variety of shapes and sizes in accordance with this disclosure.

A non-limiting method of manufacturing biosensor 110 is described below. A roll of thermoset-adhesive coated sensor support substrate material is fed into a punching unit where notches 136, 138 and an opening is punched out giving preliminary definition to main portion 116 and sensor support substrate elements 118, 120. A separate coating step can be performed before the sensor support material substrate is fed into the punching unit It is appreciated that the sensor support substrate pre-coated with a heat-sealable adhesive also is commercially available.

The electrodes 52, 54 are formed on the electrode support substrate as described above with reference to biosensor 10. The sensor support substrate material then fed into a cutting/lamination station along with the electrode support substrate material. The electrode support substrate material is cut into strips and then aligned with the notches of the sensor support substrate. The electrode support substrate is coupled to the sensor support substrate by a pressure and heat-sealing lamination process. Specifically, the aligned material is rolled against either a hot plate or a heat roller to couple the sensor support substrate to the strips of the electrode support substrate material and form a sensor support/electrode support subassembly.

The sensor support/electrode support subassembly is then fed into a screen or stencil printer equipped with IR drying stations where tracks 160, 162 are laid down upon surface 122 of the substrate material. Tracks 160, 162 are printed and cured similarly to tracks 60, 62. Next, the sensor support/electrode support subassembly is fed into a reagent dispensing station. The reagent is applied to the array as described above with reference to biosensor 10.

A roll of cover substrate material is fed into a cutting/lamination station along with the sensor support/electrode support subassembly. The cover substrate material is cut into strips and then aligned with the main portion 116 and the pre-defined sensor support substrate elements 118, 120 to create capillary channels. The cover substrate is coupled to the sensor support substrate by a pressure and heat-sealing lamination process. Specifically, the aligned material is rolled against either a hot plate or a heat roller to couple the sensor support substrate to the strips of the cover substrate material.

Next, the assembled material is fed into a sensor punch and packaging station. In this station, the notches 184, 149 are formed in the respective cover substrate 121 and the electrode support substrate 114. The assembled material is punched to form individual biosensors 110, which are sorted and packed into vials, each closed with a stopper, to give packaged biosensor strips.

Referring now to FIG. 4, a user of biosensor 110 places a finger 109 having a blood collection incision against boundaries 151, 186 of respective notches 149, 184 at end 129. It is also appreciated, as shown by phantom arrows 188, 190, that the user can choose to place their finger against boundaries 151, 186 of respective notches 149, 184 at edges 148, 131; or 150, 133. Capillary forces pull the liquid blood sample flowing from the incision through a capillary channel formed between cover 121, support 114, and sensor support substrate elements 118, 120 toward array 56. The liquid blood wets the reagent (not shown) and engages array 56 where the electrochemical reaction takes place as described above.

Biosensor 210 is shown in FIGS. 5–7. Biosensor 210 includes a sensor support substrate 212, an electrode support 214, first electrically-conductive material 16 positioned on support 214, reagent 20 positioned on material 16, and first and second tracks 60, 62 positioned on sensor support substrate 212 and in engagement with material 16. Biosensor 210 is preferably a top-dose apparatus that is rectangular in shape. It is appreciated, however, that biosensor 210 can assume any number of shapes in accordance with this disclosure.

Support 214 is similar to electrode support substrate 14 except that it has uninterrupted edges 248, 250 and ends 244, 246. Support 214 is constructed of materials similar to electrode support substrate 14 as described above. Support 214 is metallized with material 16 on top surface 240. Referring to FIG. 5, material 16 on support 214 is disrupted by laser ablation to form electrodes 252, 254. Electrodes 252, 254 cooperate with one another to define an electrode array 256, leads 258, 260 that extend away from array 256, and contact pads 261, 263. Leads 260, 258 extend away from array 256 to the contact pads 261, 263 at respective edges 248, 250 of support 214. Reagent (not shown) extends across at least a portion of electrode array 256. In addition, it is appreciated that array 256 and contact pads 261, 263 can take on a variety of shapes and sizes and leads 258, 260 can be formed to have a variety of lengths and extend to a variety of locations to place contact pads 261, 263 in a variety of locations on support 214 in accordance with this disclosure.

Sensor support substrate 212 of biosensor 210 is similar to substrates 12, 112 except that it includes an opening 234 that extends between first and second surfaces 222, 224. See, FIGS. 5 and 7. A border 286 defines opening 234. It is appreciated that the size, shape, and position of opening 234 can vary in accordance with this disclosure. Sensor support substrate 212 is also formed to include notches 236, 238. When sensor support substrate 212 is coupled to support 214, opening 234 is spaced-apart from array 256 and notches 236, 238 are aligned with electrodes 254, 252 respectively. See FIGS. 6 and 7. It is appreciated, however, that opening 234 and notches 236, 238 can be located in a number of locations in sensor support substrate 212 so long as notches 236, 238 are aligned with contact pads 261, 263 in accordance with this disclosure. Preferably, sensor support substrate 212 is formed form materials similar to sensor support substrate 12 as described above and is coupled to support 214 with adhesive similar to the adhesive used to couple sensor support substrate 12 to electrode support substrate 14.

Referring now to FIG. 7, sensor support substrate 212 is coupled to the support 214 in a particular pattern leaving an unsealed portion 223, which extends between boundary 236 and end 244. The adhesive-coated sensor support substrate 212 and electrode support 214 inherently do not lie perfectly flat against one another, and therefore a capillary channel 272 is created by default between unsealed portions 223 of the sensor support substrate 212 and the support 214. See FIG. 6. The biosensor 214 of the present invention takes advantage of surface irregularities of the sensor support substrate 212 and support 214 and the thickness of the reagent to form capillary channel 272++++inc. by reference to move a liquid sample across the support 214 and toward the electrode array 256.

A non-limiting method of manufacturing biosensor 210 is described below. A roll of thermoset-adhesive coated sensor support substrate material is fed into a punching unit where notches 236, 238 and opening 234 are punched out. It is appreciated that a separate coating step can be performed before the sensor support material substrate is fed into the punching unit. It is appreciated that the sensor support substrate pre-coated with a heat-sealable adhesive is also commercially available.

The electrodes 252, 254 are formed on the electrode support substrate as described above with reference to biosensor 10. The sensor support substrate material then fed into a cutting/lamination station along with the electrode support substrate material. The electrode support substrate material cut into strips and then aligned with the notches and opening of the sensor support substrate. The electrode support substrate is coupled to the sensor support by a pressure and heat-sealing lamination process. Specifically, the aligned material is rolled against either a hot plate or a heat roller to couple the sensor support substrate to the strips of the electrode support substrate material and form a sensor support/electrode support subassembly.

The sensor support/electrode support subassembly is then fed a screen or stencil printer equipped with IR drying stations where tracks 60, 62 are laid down upon surface 222 of the substrate material as described above with reference to biosensor 10. Next, the sensor support/electrode support subassembly is fed into a reagent dispensing station. The reagent is applied to the array as described above with reference to biosensor 10.

Next, the assembled material is fed into a sensor punch and packaging station. In this station, the assembled material is punched to form individual biosensors 210, which are sorted and packed into vials, each closed with a stopper, to give packaged biosensor strips.

In use, a user of biosensor 210 places a finger into opening 234 and deposits a liquid blood sample. Capillary forces pull the liquid sample through the channel 272 created by unsealed portion 223 toward array 256. The liquid blood sample wets the reagent (not shown) and engages the electrode array 256, where the electrochemical reaction takes place as previously described.

Biosensor 310 is shown in FIGS. 8–9. Biosensor 310 includes sensor support substrate 212, electrode support 214, first electrically-conductive material 16 positioned on support 214, the reagent (not shown) positioned on material 16, and first and second tracks 60, 62 positioned on sensor support substrate 212 and in engagement with material 16. Biosensor 310 is preferably a top-dose apparatus that is rectangular in shape. It is appreciated, however, that biosensor 310 can assume any number of shapes in accordance with this disclosure.

Biosensor 310 is similar to biosensor 210 except that the electrically conductive material 16 on support 214 is disrupted by laser ablation to form electrodes 352, 354. Electrodes 352, 354 cooperate with one another to define spaced-apart electrode arrays 356, 258, leads 360, 362 that extend away from arrays 356, 358, and contact pads 361, 363. Leads 360, 362 extend away from arrays 356, 358 to contact pads 361, 363 at respective edges 248, 250 of support 214. The reagent (not shown) is positioned to extend across electrode array 356. In addition, it is appreciated that arrays 356, 358 can take on a variety of shapes and sizes and leads 360, 362 be formed to have a variety of lengths and extend to a variety of locations on support 214 in accordance with this disclosure.

Biosensor 310 is manufactured similarly to biosensor 210, except for the step of ablating the electrically conductive material 16 from the electrode support 214. To form electrodes 352, 354, the metallic layer of the metallized film is ablated in a pre-determined electrode pattern, to form arrays 356, 358, leads 360, 362 that extend from arrays 356, 358, and contact pads 361, 363. As with biosensor 10, 110, 210, the assembled material is fed into a sensor punch and packaging station. In this station, the assembled material is punched to form individual biosensors 310, which are sorted and packed into vials, each closed with a stopper, to give packaged biosensor strips.

In use, a user of biosensor 310 places a finger into opening 234 and deposits a liquid blood sample onto array 358. Capillary forces pull the liquid sample through the channel 272, across array 358 where interference corrections may be made and toward array 356. The liquid blood sample wets the reagent (not shown) and engages electrode array 356, where an electrochemical reaction takes place as previously described.

The processes and products described above include disposable biosensors 10, 110, 210, 310, especially for use in diagnostic devices. Also included, however, are electrochemical sensors for non-diagnostic uses, such as measuring an analyte in any biological, environmental, or other sample. As discussed above, biosensors 10, 110, 210, 310 can be manufactured in a variety of shapes and sizes and be used to perform a variety of assays, non-limiting examples of which include current, charge, impedance conductance, potential or other electrochemical indicative property of the sample applied to biosensor.

Although the invention has been described in detail with reference to a preferred embodiment, variations and modifications exist within the scope and spirit of the invention, on as described and defined in the following claims.

What is claimed is:

1. An electrochemical biosensor comprising:
   an electrode support substrate,
   electrodes positioned on the electrode support substrate,
   a sensor support substrate coupled to the electrode support substrate, the sensor support substrate having a first surface, and opposite second surface facing the electrode support substrate, and notches extending between the first and second surfaces, each notch being aligned with a portion of one electrode,
   a capillary channel, at least a portion of the electrodes being positioned in the capillary channel, and
   electrically conductive tracks positioned on the first surface of the sensor support substrate, a portion of each track extending from the first surface into at least one notch and being in electrical communication with one of the electrodes.

2. The biosensor of claim 1 wherein the electrodes cooperate to define an electrode array and leads extending from the array and each notch is aligned with at least a portion of one lead.

3. The biosensor of claim 1 wherein the electrodes cooperate to define spaced-apart electrode arrays.

4. The biosensor of claim 3 wherein the sensor support substrate is formed to include an opening in alignment with one of the electrode arrays.

5. The biosensor of claim 1 wherein the tracks are formed to include layers.

6. The biosensor of claim 5 wherein one layer is silver ink.

7. The biosensor of claim 5 wherein one layer is carbon ink.

8. The biosensor of claim 5 wherein the electrodes are gold.

9. The biosensor of claim 1 wherein the sensor support substrate is formed to include an opening in alignment with at least a portion of the electrodes.

10. The biosensor of claim 9 further comprising a cover substrate coupled to the sensor support substrate.

11. The biosensor of claim 10 wherein the cover substrate, sensor support substrate, and electrode support substrate cooperate with one another to define channel.

12. The biosensor of claim 1 wherein the electrode support substrate and the sensor support substrate cooperate to define the channel.

13. A biosensor comprising:
   a metallized electrode support substrate being formed to define an electrode array and leads extending from the array,
   a sensor support substrate coupled to the electrode support substrate, the sensor support substrate being formed to include notches and an opening, at least a portion of each notch being aligned with one lead and the opening being spaced-apart from the leads, and
   electrically conductive tracks positioned on the sensor support substrate, each track extending across one of the notches and into engagement with one lead.

14. The biosensor of claim 13 wherein the tracks are formed to include layers.

15. The biosensor of claim 14 wherein one layer is silver ink.

16. The biosensor of claim 14 wherein one layer is carbon ink.

17. The biosensor of claim 14 wherein the electrode array and leads are gold.

18. The biosensor of claim 14 further comprising a cover substrate coupled to the sensor support substrate and extending across the electrode array.

19. A biosensor comprising:
   an electrode support substrate being formed to define an electrode array and leads extending from the array,
   a sensor support substrate positioned on the electrode support substrate, the sensor support substrate being formed to include notches and an opening, at least a portion of each notch being aligned with one lead and the opening being spaced-apart from the leads, and
   electrically conductive tracks positioned on the sensor support substrate, each track extending across one of the notches and into engagement with one lead.

20. The biosensor of claim 19 wherein the tracks are formed to include layers.

21. The biosensor of claim 20 wherein one layer is silver ink.

22. The biosensor of claim 20 wherein one layer is carbon ink.

23. The biosensor of claim 20 wherein the electrode array and leads are gold.

24. The biosensor of claim 20 further comprising a cover substrate coupled to the sensor support substrate and extending across the electrode array.

* * * * *